(12) United States Patent
Caprio

(10) Patent No.: US 10,568,847 B2
(45) Date of Patent: Feb. 25, 2020

(54) COMPOSITIONS AND METHODS FOR TREATMENT OF ERECTILE DYSFUNCTION

(71) Applicant: James J. Caprio, Weston, FL (US)

(72) Inventor: James J. Caprio, Weston, FL (US)

( * ) Notice: Subject to any disclaimer, the term of this patent is extended or adjusted under 35 U.S.C. 154(b) by 180 days.

(21) Appl. No.: 15/434,226

(22) Filed: Feb. 16, 2017

(65) Prior Publication Data

US 2018/0161284 A1    Jun. 14, 2018

Related U.S. Application Data

(60) Provisional application No. 62/433,502, filed on Dec. 13, 2016.

(51) Int. Cl.
| | |
|---|---|
| *A61K 36/18* | (2006.01) |
| *A61K 31/05* | (2006.01) |
| *A61K 31/352* | (2006.01) |
| *A61K 36/185* | (2006.01) |
| *A61K 45/06* | (2006.01) |

(52) U.S. Cl.
CPC ............ *A61K 31/05* (2013.01); *A61K 31/352* (2013.01); *A61K 36/185* (2013.01); *A61K 45/06* (2013.01)

(58) Field of Classification Search
CPC ...................................................... A61K 36/18
See application file for complete search history.

(56) References Cited

U.S. PATENT DOCUMENTS 6,469,012 B1 * 10/2002 Ellis .................... A61K 31/535
514/234.5

FOREIGN PATENT DOCUMENTS

WO    WO-2016098112 A1 *  6/2016  ........... A61K 9/0034

OTHER PUBLICATIONS

De Veij et al., "Detection of counterfeit Viagra® with Raman spectroscopy," Journal of Pharaceutical and Biomedical Analysis 46:303-309, 2008.*

* cited by examiner

*Primary Examiner* — Rosanne Kosson
(74) *Attorney, Agent, or Firm* — Rafael Perez-Pineiro; The Brickell IP Group, PLLC

(57) ABSTRACT

The subject invention pertains to methods and compositions for the treatment of erectile dysfunction (ED) (e.g., impotence) in a subject in need thereof utilizing one or more cannabinoid and one or more anti-ED drug.

6 Claims, No Drawings

COMPOSITIONS AND METHODS FOR TREATMENT OF ERECTILE DYSFUNCTION

CROSS-REFERENCE TO RELATED APPLICATION

This application claims benefit from U.S. Provisional Patent Application No. 62/433,502, entitled "Compositions and Methods for Treatment of Erectile Dysfunction," filed on Dec. 13, 2016, which is hereby incorporated in its entirety by reference.

BACKGROUND

Erectile dysfunction (ED) or impotence is a sexual dysfunction characterized by the inability to develop or maintain an erection of the penis during sexual activity. A penile erection is the hydraulic effect of blood entering and being retained in sponge-like bodies within the penis. The process is most often initiated as a result of sexual arousal, when signals are transmitted from the brain to nerves in the penis. The most important organic causes are cardiovascular disease and diabetes, neurological problems (for example, trauma from prostatectomy surgery), hormonal insufficiencies (hypogonadism) and drug side effects.

The study of ED within medicine is covered by andrology, a sub-field within urology. Research indicates that ED is common, and it is suggested that approximately 40% of males suffer from ED or impotence, at least occasionally. Current treatments for ED include drugs such as, for example, vardenafil, avanafil, sildenafil, tadalafil, and alprostadil. Furthermore, there are studies suggesting that natural herbals, such as damiana, horny goat weed, and yohimbine, are also effective in treating ED.

BRIEF SUMMARY

In one aspect, the subject disclosure provides methods for treatment and/or prevention of erectile dysfunction (ED) in a subject in need thereof. One advantage of the invention is that it reduces or eliminates side effects experienced by users of AEDs, such as for example, headache, dizziness, etc.

In some embodiments, cannabis, or extract thereof, is administered in an amount from about 5 mg to about 50 mg.

In another aspect, the subject disclosure provides a composition for treatment of ED. The composition may comprise a therapeutically effective amount of an anti-erectile dysfunction drug (AED), or pharmaceutically acceptable salt thereof; and cannabis, or an extract thereof.

In some embodiments of the aspects described, the AED may comprise vardenafil, avanafil, sildenafil, tadalafil, alprostadil, damiana, horny goat weed, and/or yohimbine.

In some embodiments, the cannabis extract comprises at least one cannabinoid. In some embodiments, the cannabis extract comprises cannabidiol (CBD). In some embodiments, the cannabis extract comprises cannabinoid tetrahydrocannabinol (THC). In some embodiments, the cannabis extract comprises cannabidiolic acid (CBDA). In some embodiments, the cannabis extract comprises cannabidivarin (CBDV). In some embodiments, the cannabis extract comprises cannabidivarinic acid (CBDVA). In some embodiments, the cannabis extract comprises tetrahydrocannabinol (THC).

In another aspect, the subject disclosure provides a pharmaceutical composition comprising a therapeutically effective amount of an anti-erectile dysfunction drug (AED), or pharmaceutically acceptable salt thereof; and cannabis, or an extract thereof; and a pharmaceutically acceptable carrier. In some embodiments, the cannabis, or extract thereof, concentration is from about 5 mg to about 50 mg.

DETAILED DISCLOSURE

The present disclosure pertains to compositions and methods for the treatment and/or prevention of erectile dysfunction (ED).

Several aspects of the disclosure are described below, with reference to examples for illustrative purposes only. It should be understood that numerous specific details, relationships, and methods are set forth to provide a full understanding of the disclosure. One having ordinary skill in the relevant art, however, will readily recognize that the aspects described can be practiced without one or more of the specific details or practiced with other methods, protocols, reagents, and animals. The aspects described are not limited by the illustrated ordering of acts or events, as some acts may occur in different orders and/or concurrently with other acts or events. Furthermore, not all illustrated acts, steps or events are required to implement a methodology in accordance with the aspects described. Many of the techniques and procedures described, or referenced herein, are well understood and commonly employed using conventional methodology by those skilled in the art.

Prior to setting forth aspects of the disclosure in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as defined above for "and/or". For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. As such, a "subject" includes an animal that is being treated for erectile dysfunction, or the recipient of a mixture of components or compositions as described herein. The term "animal," includes, but is not limited to, a mammal, such as a mouse, rat, dog, guinea pig, cow, horse, chicken, cat, rabbit, pig, monkey, chimpanzee, and human.

The term "effective amount" or "therapeutically effective amount" means that amount of active compound that elicits the biological or medicinal response in a tissue system, animal or human that is being sought by a researcher, veterinarian, medical doctor or other clinician, which includes alleviation of one or more of the symptoms of the disease or disorder being treated; reduction of the severity of one or more of the symptoms of the disease or disorder being treated; or otherwise provides the desired effect. The precise dosage will vary according to a variety of factors such as subject-dependent variables (e.g., age, medical history, etc.), the disorder or condition, and the treatment being affected. In particular aspects of the present disclosure directed to co-therapy or combination therapy, comprising administration of one or more anti-ED agents and a *cannabis* extract or one or more cannabinoids (or synthetic variants thereof), therapeutically effective amount means that amount of the combination of agents taken together so that the combined effect elicits the desired biological or medicinal response. For example, the therapeutically effective amount of co-therapy comprising administration of an anti-ED agent and a cannabinoid would be the amount of the cannabinoid and the amount of the suitable anti-ED agent that, when taken together or sequentially, have a combined effect that is therapeutically effective. Further, it will be recognized by one skilled in the art that in the case of co-therapy with a therapeutically effective amount, as in the example above, the amount of cannabinoid or the amount of the suitable anti-ED agent individually may or may not be therapeutically effective.

The term "pharmaceutically acceptable," as used herein, means approved by a regulatory agency of the Federal or a state government or listed in the U.S. Pharmacopeia or other generally recognized pharmacopeia for use in animals and/or in humans.

"Pharmaceutically acceptable salt" refers to a salt of a compound of the disclosure that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

Aspects of the present disclosure provide compositions comprising the following active ingredients: *cannabis*, a *cannabis* extract, or one or more cannabinoid (or synthetic variant thereof); and one or more anti-ED agents. The compositions described can also be in the form of a pharmaceutical composition comprising one or more pharmaceutically acceptable carriers described herein. The compounds and compositions of the disclosure can be used to treat, alleviate, inhibit or prevent ED. In some embodiments, the *cannabis*, or extract thereof, concentration is from about 5 mg to about 50 mg. For example, THC in a concentration from about 5 mg to about 50 mg may be used or provided.

The term "carrier" refers to a diluent, adjuvant, excipient, and/or vehicle with which the compositions are administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition(s) may also contain wetting or emulsifying agents or suspending/diluting agents, or pH buffering agents, or agents for modifying or maintaining the rate of release of the formulations. The compositions can take the form of solutions, suspensions, emulsion, tablets, pills, capsules, powders, gels, creams, cigar/cigarette, sustained-release formulations and the like. Formulations can include standard carriers such as pharmaceutical grades of mannitol, lactose, sodium saccharine, starch, magnesium stearate, cellulose, magnesium carbonate, etc. Such compositions will contain an effective amount of the active ingredient(s) together with a suitable amount of carrier so as to provide the proper form to the subject based on the mode of administration to be used.

If for intravenous administration, the compositions are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachette indicating the amount of active agents. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

Moreover, if a packaging material is utilized to package the composition, it may be biologically inert or lack bioactivity, such as plastic polymers, silicone, etc. and may be processed internally by the subject without affecting the effectiveness of the components packaged and/or delivered therewith. Additionally, the compositions and components may be packaged with additional agents.

In some embodiments, the compositions comprise *cannabis*, in whole or in part, from the bud of a marijuana plant. In other embodiments, the compositions comprise an extract of *cannabis*. The extract may comprise one or more cannabinoid selected from cannabidiol (CBD), tetrahydrocannabinol (THC), cannabidiolic acid (CBDA), cannabidivarin (CBDV), and cannabidivarinic acid (CBDVA). Alternatively, one or more of the cannabinoids may be utilized in the methods and compositions provided in an isolated or purified form. Further, synthetic variants of the cannabinoids may be utilized, either individually or in combination with other synthetic cannabinoid variants or in combination with non-synthetic cannabinoids.

In some embodiments, the cannabinoid used is in the form of a highly purified extract of *cannabis* such that the cannabinoid is present at greater than 98% of the total extract (w/w). In some embodiments, the cannabinoid tetrahydrocannabinol (THC) has been substantially removed, to a level of not more than 0.15% (w/w). Alternatively, the cannabinoid may be a synthetically produced cannabinoid.

In some embodiments, the compositions also comprise an anti-ED drug (or extract). The anti-ED drug may include one or more of vardenafil, avanafil, sildenafil, tadalafil, and alprostadil. The anti-ED drug/extract may also include one or more extracts of damiana, horny goat weed, and yohimbine. Damiana, horny goat weed, and yohimbine may be utilized in the compositions and methods described as either liquid extracts, dried powders, or lyophilized extracts. Alternatively, purified extracts comprising the active ingredients from one or more of each of damiana, horny goat weed (e.g., epimedium), and yohimbine may be utilized. Likewise, synthetic variants of the active ingredients from one or more of damiana, horny goat weed, and yohimbine may be utilized in the compositions and methods described. The synthetic variants can also be utilized in combination with one or more purified extracts.

Aspects of the present disclosure also provide kits comprising one or more *cannabis* extract or cannabinoid-anti-ED formulations, or individual formulations, as described herein. The kits may further be used in the methods described herein. The kits may also include at least one reagent and/or instructions for their use. Also, the kit may include one or more containers filled with reagent(s) and/or one or more components of the disclosure. One or more container of the kits provided may also comprise a cannabinoid, preferably in a purified form. One or more container of the kits provided may alternatively comprise a *cannabis* extract. Also, one or more container of the kits provided may also comprise an anti-ED agent, preferably in a purified form. In some embodiments, the *cannabis* extract or cannabinoid and anti-ED agent may be provided in separate containers for mixing prior to use, or for individual ingestion/administration. The kits may also comprise a control composition, such as reagents that lack a cannabinoid (or synthetic variant) and/or anti-ED agent for use as a control reagent in experimentation. As it would be understood by those skilled in the art, detection or labeling methodologies can be used in the kits provided when utilized in an experimental or laboratory setting.

Aspects of the present disclosure are further directed to methods of treatment/prevention which involve administering therapeutically effective amounts of a *cannabis* extract or one or more cannabinoid (or synthetic variant thereof) and an anti-ED agent, or pharmaceutical compositions of the present disclosure, to a subject, preferably a mammal, and most preferably a human, for treating and/or preventing erectile dysfunction (e.g, impotence). In some embodiments, the *cannabis*, or extract thereof, concentration utilized in the methods described is from about 5 mg to about 50 mg. For example, THC in a concentration from about 5 mg to about 50 mg may be used or provided.

"Preventing" or "prevention" refers to a reduction in risk of acquiring disorder (i.e., causing at least one of the clinical symptoms of the disease/disorder not to develop in a subject that may be predisposed to the disorder but does not yet experience or display symptoms of the disorder).

"Treating" or "treatment" of any disorder refers, in one embodiment, to ameliorating the disorder (i.e., arresting or reducing the development of the disorder (i.e., impotence) or at least one of the clinical symptoms thereof). In another embodiment "treating" or "treatment" refers to ameliorating at least one physical parameter, which may not be discernible by the subject. In yet another embodiment, "treating" or "treatment" refers to modulating the disorder, either physically, (e.g., stabilization of a discernible symptom), physiologically, (e.g., stabilization of a physical parameter), or both. In yet another embodiment, "treating" or "treatment" refers to delaying the onset of the disorder.

Administration can be locally (confined to an area of body) and/or systemically in the subject. It may be desirable to administer the *cannabis* extract or cannabinoid/anti-ED agent combination, or pharmaceutical compositions comprising same, locally to the area in need of treatment, such as the groin rejoin or penis. This method of administration may be achieved by, for example, and not by way of limitation, local infusion, topical application, by injection, by catheter, or by means of an implant (e.g., a porous membrane). Administration may also be orally, such as but not limited to, by way of pills, capsules, liquid, vapors, or smoking.

It is also understood and contemplated that aspects of this disclosure can provide more than two active ingredient components in the mixtures of compositions herein disclosed. Also, the disclosed methods can comprise the simultaneous or separate administration of multiple active ingredients. Thus, embodiments may further include the administration of a third, fourth, etc. active ingredient, wherein the third, fourth, etc. active ingredient is administered separately, but at the same time as the other active ingredients, or hours or days after the first administration of active ingredients.

In some embodiments, the *cannabis* extract or cannabinoid(s) and anti-ED agent(s), or pharmaceutical composition containing them, can be delivered in a controlled release system. Such methods may include the use of a pump for administration (e.g., use of an intravenous drip). In another embodiment, a controlled release system can be placed in the proximity of the therapeutic target (e.g., groin or penis), requiring only a fraction of the dose required if dosed systemically.

The compounds and compositions of the invention may also be utilized in pharmaceutically acceptable compositions in the methods provided herein.

It would also be understood by a skilled artisan how to use the compositions described herein for therapeutic purposes without undue experimentation based on the teachings provided throughout the specification.

The amount of active ingredients or pharmaceutical compounds of the invention which will be effective in the treatment, inhibition and/or prevention of ED can be determined by standard clinical techniques. Additionally, in vitro assays may be employed to help identify optimal dosage ranges. The precise dose to be utilized will also depend on the route of administration, and the seriousness of the ED, and should also be decided according to the sound medical judgment of the clinician and each patient's individual circumstances. The specific therapeutically effective dosage level for any particular patient will depend upon a variety of factors including: the type and degree of the response to be achieved; the specific composition and other agent(s), if any, employed; the age, weight, general health, sex and diet of the patient; the time of administration, route of administration, and rate of excretion of the composition; the duration of the treatment; other drugs used in combination or coincidental with the composition; and any other factors well known in the medical arts. Effective dosages may also be extrapolated from dose-response curves derived from in vitro or animal model testing systems.

All patents, patent applications, provisional applications, and publications referred to or cited herein are incorporated by reference in their entirety, including all figures and tables, to the extent they are not inconsistent with the explicit teachings of this specification. By citation of various references in this document, Applicants do not admit any particular reference is "prior art" to their invention.

I claim:

1. A composition for the treatment of erectile dysfunction, comprising a therapeutically effective amount of sildenafil and a therapeutically effective amount of *cannabis* extract, wherein the *cannabis* extract comprises from about 5 mg to about 50 mg tetrahydrocannabinol.

2. A pharmaceutical composition for treatment of erectile dysfunction, comprising a therapeutically effective amount of sildenafil; about 5 mg to about 50 mg tetrahydrocannabinol; and a pharmaceutically acceptable carrier.

3. The composition of claim 1, wherein the composition is in an oral dosage form.

4. The composition of claim 3, wherein the oral dosage form is selected from a pill, a capsule, and a liquid form.

5. The pharmaceutical composition of claim 2, wherein the composition is in an oral dosage form.

6. The pharmaceutical composition of claim 5, wherein the oral dosage form is selected from a pill, a capsule, and a liquid form.

* * * * *